United States Patent
Voorhees-Nordhaus et al.

(10) Patent No.: US 11,642,287 B2
(45) Date of Patent: May 9, 2023

(54) POWDER COMPOSITIONS HAVING REDUCED FRAGILITY

(71) Applicant: L'OREAL, Paris (FR)

(72) Inventors: Lisa A. Voorhees-Nordhaus, Middlesex, NJ (US); Hubert Tunchiao Lam, Berkeley Heights, NJ (US); Cristina Dubceac, Fremont, CA (US)

(73) Assignee: L'OREAL, Paris (FR)

( * ) Notice: Subject to any disclaimer, the term of this patent is extended or adjusted under 35 U.S.C. 154(b) by 47 days.

(21) Appl. No.: 16/804,218

(22) Filed: Feb. 28, 2020

(65) Prior Publication Data
US 2021/0267850 A1    Sep. 2, 2021

(51) Int. Cl.
| | |
|---|---|
| *A61K 8/02* | (2006.01) |
| *A61K 8/25* | (2006.01) |
| *A61K 8/29* | (2006.01) |
| *A61K 8/36* | (2006.01) |
| *A61K 8/34* | (2006.01) |
| *A61K 8/58* | (2006.01) |
| *A61Q 1/10* | (2006.01) |
| *A61Q 1/12* | (2006.01) |
| *A61K 8/365* | (2006.01) |

(52) U.S. Cl.
CPC .............. *A61K 8/022* (2013.01); *A61K 8/25* (2013.01); *A61K 8/29* (2013.01); *A61K 8/342* (2013.01); *A61K 8/361* (2013.01); *A61K 8/365* (2013.01); *A61K 8/585* (2013.01); *A61Q 1/10* (2013.01); *A61Q 1/12* (2013.01); *A61K 2800/623* (2013.01)

(58) Field of Classification Search
None
See application file for complete search history.

(56) References Cited

U.S. PATENT DOCUMENTS

| | | | |
|---|---|---|---|
| 8,753,684 B2 | 6/2014 | Pfluecker et al. | |
| 9,254,398 B2 | 2/2016 | Schlossman et al. | |
| 9,655,835 B2 | 5/2017 | Finjan et al. | |
| 9,931,285 B2 | 4/2018 | Jansen et al. | |
| 2005/0074474 A1* | 4/2005 | Sako | A61K 8/676 424/401 |
| 2005/0187128 A1* | 8/2005 | Martin | A61Q 1/12 510/392 |
| 2016/0101033 A1 | 4/2016 | Finjan et al. | |
| 2016/0213578 A1* | 7/2016 | Schlossman | C09C 1/3669 |

FOREIGN PATENT DOCUMENTS

| | | |
|---|---|---|
| EP | 3270871 B1 | 7/2019 |
| JP | 2016153437 A | 8/2016 |
| WO | 2010111279 A1 | 9/2010 |
| WO | 2018069204 A1 | 4/2018 |

OTHER PUBLICATIONS

Powder Bronzer, Mintel GNPD, Record ID 5480321, p. 1-2, Published on Feb. 2018.
M.A.C. Strobe Tone-Up Cushion Compact SPF 50/PA++++, Mintel GNPD, Record ID 5781701, p. 1-5, Published on Jun. 2018.
Etude House Lovely Cookie Blusher, Mintel GNPD, Record ID 6383579, p. 1-4, Published on Mar. 2019.
French Search Report and Written Opinion dated Dec. 17, 2020 in French Patent No. 2003573, 9 pages.
Database GNPD, Mintel: Dec. 8, 2016, anonymous "personal color palette", XP055793293, database accession No. 4393115.

* cited by examiner

*Primary Examiner* — Melissa L Fisher
(74) *Attorney, Agent, or Firm* — Meagher Emanuel Laks Goldberg & Liao, LLP

(57) ABSTRACT

Pressed powder compositions are provided. The compositions include at least about 80% by weight of a mineral portion. The mineral portion comprises at least one alkylsilane-coated mineral; polyhydroxystearic acid, synthetic mica, and less than about 12% by weight of binding agents. Methods of shadowing the eyes and methods of forming pressed powder compositions are also provided.

10 Claims, No Drawings

POWDER COMPOSITIONS HAVING REDUCED FRAGILITY

FIELD OF THE INVENTION

The present invention relates to cosmetic compositions in the form of a pressed powder that include at least one alkyl-silane coated mineral and polyhydroxystearic acid and, in particular, such compositions having reduced fragility.

DISCUSSION OF THE BACKGROUND

Pressed powder compositions for use on the skin are known. Such compositions take the form of a solid mass and may include various pigments, oils, waxes, polymers, and the like. A user applies the product to her face, eyelids, etc., such as with a cosmetic brush or applicator. Some compositions, particularly for eyeshadows, utilize high loading of certain minerals in order to provide intense color "payoff." However, the inventors have found that pressed powder compositions that have loading of certain minerals (and typically low levels of binders) are susceptible to mechanical failure such cracking when the product is dropped such as during shipping.

The present inventors have recognized the need to solve the above-mentioned drawback while still maintaining product benefits such as color payoff, texture, and aesthetics.

SUMMARY OF THE INVENTION

According to one aspect, the present invention relates to compositions in the form of a pressed powder. The pressed powder compositions include at least about 80% by weight of a mineral portion. The mineral portion includes at least one alkylsilane-coated mineral. The composition further includes polyhydroxystearic acid and synthetic mica. The compositions have less than about 12% by weight of binding agents.

According to another aspect of the invention, the present invention relates to compositions in the form of a pressed powder. The pressed powder compositions include at least about 80% by weight of a mineral portion. The mineral portion includes at least one triethoxycaprylylsilane-coated mineral having a substrate selected from a group consisting of iron oxide, titanium dioxide, talc, and combinations thereof. The composition further includes polyhydroxystearic acid. The pressed powder compositions have less than about 12% by weight of binding agents that are selected from a group consisting of fatty compounds, water, fatty acid salts, and glycols. The pressed powder composition comprises at least about 11% of a combined weight percentage of minerals having substrates selected from titanium dioxide and iron oxide.

According to another aspect of the invention, the present invention relates to methods of shadowing the eyes. The method includes applying the above described pressed powders to eyelids or skin around the eyes.

According to another aspect of the invention, a method of making a pressed powder includes the step of adding polyhydroxystearic acid to a powder portion wherein the powder portion comprises at least one mineral coated with alkylsilane to form a powder-binder composition; and mechanically pressing the powder-binder composition without previously heating the powder-binder composition to a temperature of at least 50° C.

DETAILED DESCRIPTION OF THE INVENTION

As used herein, the expression "at least one" means one or more and thus includes individual components as well as mixtures/combinations.

As used herein, all ranges provided are meant to include every specific range within, and combination of sub ranges between, the given ranges. Furthermore, notably the range description of the type "from 1%, 2% or 5% to about 10%, 15%, or 20% by weight," includes 1%-10%, 1%-15%, 1%-20%, 2%-10%, 2%-15%, 2%-20%, 5%-10%, 5%-15%, and/or 5%-20%. Other than in the operating examples, or where otherwise indicated, all numbers expressing quantities of ingredients and/or reaction conditions are to be understood as being modified in all instances by the term "about," meaning within 10% to 15% of the indicated number.

"Actives basis" as used herein means considering only the particular component of ingredient (e.g., in a composition) and ignoring other chemically unrelated components that may be also be present in the same raw material source of that particular component.

"Polymer" as used herein means a compound which is made up of at least two monomers.

"Keratinous materials" includes materials containing keratin such as hair, skin, eyebrows, lips and nails.

"Solids basis" as used herein means considering only components (e.g., in a composition) that are solid at room temperature and ignoring portions of the composition that are liquid, e.g., water and other volatile solvents.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, hydroxyalkyl groups, and polysiloxane groups. The substituent(s) may be further substituted.

"Volatile", as used herein, means having a flash point of less than about 100° C.

"Non-volatile", as used herein, means having a flash point of greater than about 100° C.

"About," as used herein, when referring to concentrations of various ingredients or components means within 10% or within about 15% of the stated number. For example, about 10% means from 8.5% to 11.5%, such as between 9% and 11%.

"Anhydrous" means the compositions contain less than about 2% by weight of water, such as less about 1% water, such as less than about 0.5% water such as less about 0.1% of water.

All percentages of ingredients herein are listed on an actives basis unless specifically stated otherwise. Further, all percentages of ingredients are percent by weight unless specifically stated otherwise.

The composition of the present invention is generally in the form of a pressed powder, i.e., a composition including powders which have been densified using, for example, mechanical forces.

The compositions and methods of the present invention can comprise, consist of, or consist essentially of the essential elements and limitations of the invention described herein, as well as any additional or optional ingredients, components, or limitations described herein or otherwise useful in personal care. In certain embodiments, compositions of the present invention are anhydrous.

Mineral Portion

Compositions of the present invention include a mineral portion. As one skilled in the art will readily recognize, "mineral portion" means the portion of the composition that consists of one or more minerals as well surface treatments/coatings directly formed thereon. By "mineral" it is meant any minerals that remain finely divided in the composition, such as on the order of a nanometer to 1000 microns.

Furthermore, pressed powder compositions of the present invention include at least about 80% by weight of the mineral portion (and, accordingly, less than about 20% by weight of ingredients that are not minerals, as described below). According to certain embodiments of the invention, the weight percentage of the mineral portion in the pressed powder is from about 70%, 80% by weight to about 85%, 90% or 95% by weight.

Minerals suitable for use in the present invention generally comprise or consist of a mineral having a substrate which is predominantly or entirely inorganic. The mineral substrate may be a conventional mineral—an element or compound, amorphous or crystalline, formed through biogeochemical processes or alternatively a similar material that is produced synthetically. Suitable mineral substrates include various oxides, silica, silicates (including aluminosilicates, including lapis lazuli/ultramarine pigment).

According to certain embodiments, the mineral portion includes pigments that function primarily to provide color, i.e., "color pigments," (e.g., iron oxides, pearlescent/effect pigments including multilayer pearlescent pigments based on synthetic fluorophlogopites, ultramarines). The mineral portion may also include minerals that function primarily to provide other properties such as coverage, whiteness, opacity, UV-absorption/scattering, and texture ("other minerals"—e.g., non-pearlescent talcs and micas, titanium dioxide, zinc oxide, synthetic mica). According to certain embodiments, the fraction of the mineral portion that consists of color pigments is at least about 50%, such as at least about 70%).

Pearlescent pigments are pigments that generally have or approach the luster of natural pearls. Typically, these particulates are plate-like with the broad face of the platelets ranging from about 4 microns to about 1,000 microns across and about 0.5 micron thick. One class of suitable pearlescent pigments include particulates having a mica, synthetic mica, or synthetic fluorophlogopite substrate having one or more inorganic coatings formed thereon including: a titanium-containing (e.g., titanium oxide) coating, an iron oxide coating, a tin oxide coating, a chromium oxide coating, and/or an iron blue coating. Another class of suitable pearlescent pigments are those of bismuth oxychloride.

The inventors have found that, according to certain embodiments, in order to deliver intense color, the minerals are selected such that the combined weight percentage of minerals have substrates selected from titanium dioxide and iron oxide is at least about 11% by weight, such as at least about 15% by weight, such as from about 11%, or 15% or 20% to about 20%, 25%, 30%, 50% or 60%.

The substrate of the various minerals may have an average (mean or median) particle size that ranges between about 1 nanometer (nm) to about 500 microns. According to certain embodiments, the average primary particle size ranges from about 1 micron to about 200 microns, such as from about 1 micron to about 150 microns. According to certain embodiments, the minerals (e.g., a micronized metal oxide) may have a primary particle size of about 5 nm to about 150 nm if the particles are spherical or granular. If the particles are acicular the primary particle size may be about 5 nm to about 50 nm by about 50 nm to 150 nm. Primary particle size may be analyzed using transmission electron microscopy.

The mineral substrate may, according to certain embodiments have a surface treatment such as a coating formed thereon. The coating may be inorganic, organic, organosilicone, or combinations thereof. At least one of the minerals in the mineral portion is an alkylsilane-coated mineral. In certain embodiments, at least one of the minerals in the mineral portion is a synthetic mica.

Synthetic Mica

Pressed powder compositions of the present invention desirably include at least one synthetic mica. By "synthetic mica" it is meant a class of synthetic aluminosilicate minerals. Other names for synthetic mica include synthetic fluorine mica, fluorphlogopite, fluorphlogopite mica, artificial mica, or synthetic mica crystal. The inventors have found that synthetic mica is particularly helpful in providing compositions of the present invention to have an intense color deposit in combination with reduced fragility. Synthetic micas useful in compositions of the present invention include synthetic mica with no coatings or surface treatments as well as synthetic micas having one or more metal oxide coatings (e.g., titanium dioxide, silica, and/or iron oxide) such as may be used to form a pearlescent pigment having a synthetic mica substrate. According to certain embodiments, the concentration of synthetic mica in the composition is from about 2%, 5%, 10%, or 15% to about 15%, 20%, 30%, or 50%.

Alkylsilane-Coated Mineral

Pressed powder compositions of the present invention include at least one alkylsilane-coated mineral. The alkylsilane-coated mineral includes a mineral substrate having an alkylsilane coating formed thereon. As well understood by those skilled in the art, an alkylsilane coating is characterized as having an oxygen atom associated with the substrate that is bonded to a silicon atom. The silicon atom is further bonded to at least one group having alkyl $[(CH_2)_n]$ functionality. The length of the alkyl group (n) may range from 1 to 50, such as from 1 to 20, such as from 2 to 15. The alkylsilane may be an alkylsilane or more specifically an alkoxysilane, such as a trialkoxyalkylsilane. The silicon atom may be further bonded to other alkylsilane groups, alkoxy groups, or other organosilane groups. A notable alkylsilane is caprylylsilane such as triethoxycaprylylsilane. The alkylsilane coating is formed on the mineral substrate by processes known to those skilled in the art such as chemically reacting an alkoxysilane with the mineral substrate to be coated in a solvent-based process, as described in U.S. Pat. No. 9,254,398B2, issued Feb. 9, 2016 and assigned to Kobo Products, Inc. and entitled, "Self-Dispersible Coated Metal Oxide Powder, And Process for Production and Use".

In certain embodiments, the mineral substrate having the alkylsilane-coating formed thereon is selected from an iron oxide, a zinc oxide, a titanium oxide, a talc, a borosilicate (e.g., calcium borosilicate), a natural mica, a synthetic mica, a silica, or combinations thereof. According to certain other embodiments, the mineral substrate having the alkylsilane-coating formed thereon is selected from iron oxide, titanium dioxide, talc, and combinations thereof.

The concentration by weight of the alkylsilane relative to the entire pressed powder composition may range from about 0.1%, 0.25%, 0.5% or 0.75% to about 1%, 2%, 3% or 5% by weight. In one notable example, the concentration by weight of the alkylsilane relative to the entire pressed powder composition is less than 1.5%, such as from 0.25% to 1.5%.

Furthermore, the concentration by weight of the alkylsilane-coated mineral relative to the entire pressed powder composition (i.e., the total weight of all minerals having an alkylsilane coating formed thereon, including the corresponding mineral substrates, divided by the total weight of composition) may be at least about 5% by weight. In other embodiments, the concentration by weight of the alkylsilane-coated mineral relative to the entire pressed powder composition is from about 1%, 2%, 3% or 5% to about 5%, 10%, 25%, 50% or 60% by weight. In one notable example, the concentration by weight of the alkylsilane-coated mineral is from about 5% about 50%, such as from 5% to 15%.

According to one notable embodiment, the alkylsilane-coated mineral is selected from a group consisting of an alkylsilane coated iron oxide, an alkylsilane-coated talc and an alkylsilane-coated titanium dioxide, and combinations thereof. According to another notable embodiment, the alkylsilane-coated mineral is selected from a group consisting of a triethoxycaprylylsilane-coated iron oxide, a triethoxycaprylylsilane-coated talc and a triethoxycaprylylsilane-coated titanium dioxide, and combinations thereof.

According to certain embodiments, the mineral portion includes at least one mineral substrate having multiple coatings formed thereon. For example, the mineral portion may include a mineral substrate having both an alkylsilane-coating and a coating of polyhydroxystearic acid. In this embodiment, polyhydroxystearic acid may be, in effect, formed on the alkylsilane-coated mineral.

The particular process for forming the multiple coatings may vary. For example, within the scope of "formed on the alkylsilane-coated mineral," it is contemplated that either coating may be formed on the substrate before the other, although in certain embodiments, the alkylsilane is formed first. For example, the alkylsilane may be formed on the mineral substrate.

In certain notable embodiments, the mineral substrate is selected from iron oxide, titanium dioxide, talc, natural or synthetic mica, silica, borosilicate and combinations thereof and the mineral substrate has two coatings formed thereon—an alkylsilane coating and a polyhydroxystearic acid coating.

The polyhydroxystearic acid may be co-formed with the alkyl-silane coating on a particular mineral substrate. This co-forming process may include and of various suitable methods know in the art, such as by dissolving alkylsilane in a suitable solvent, mixing in the mineral substrate, heating to remove solvent, drying, and milling. Subsequently polyhydroxystearic acid may be sprayed onto the alkylsilane coated powder, heated again to dry, and milled again.

Processes for coating mineral substrates with alkyl-silane and polyhydroxystearic acid is described in U.S. Pat. No. 9,254,398B2, issued Feb. 9, 2016 and assigned to Kobo Products, Inc. and entitled, "Self-Dispersible Coated Metal Oxide Powder, And Process for Production and Use," which is herein incorporated by reference in its entirety.

The concentration of the alkylsilane-coated minerals in the composition may be at least 5% by weight. In certain embodiments of the invention, the concentration of the alkylsilane-coated minerals in the composition ranges from about 5%, 10%, 15% or 25% to about 30%, 40%, 50%, 60% or 80% by weight. In certain of these embodiments, the alkylsilane is tricaprylylethoxysilane-coated iron oxide.

Examples of suitable alkylsilane-coated minerals include BWBO-11SP (C33-7001), BWRO-11SP (C33-8001) and BWYO-11SP (C33-9001) and TALC N-11SP, available from Kobo Products, Inc. of South Plainfield, N.J.

Polyhydroxystearic Acid

Pressed powder compositions of the present invention include polyhydroxystearic acid. Polyhydroxystearic acid is a polyester having a soft, waxy material under ambient conditions.

As discussed above the polyhydroxystearic acid may be co-formed with the alkyl-silane coating on a particular mineral substrate, such as described above. For example, the polyhydroxystearic acid in the composition may be, at least in part, formed on the alkysilane-coated mineral by drying the polyhydroxystearic acid at a high temperature, such as described in U.S. Pat. No. 9,254,398.

In alternative embodiment, the polyhydroxystearic acid may be formed on a different mineral substrate. In yet, another alternative, the polyhydroxystearic acid may be merely added directly to other cosmetic ingredients and not coated onto a mineral substrate via a separate step.

In certain embodiments, the concentration of the polyhydroxystearic acid relative to the entire pressed powder composition may range from about 0.1%, 0.25%, 0.5% or 0.75% to about 1%, 2%, 3% or 5% by weight. In one notable example, the polyhydroxystearic acid is formed on the alkysilane-coated mineral and is present in a concentration by weight of the polyhydroxystearic acid relative to the entire pressed powder composition of about 1%.

According to certain embodiments, the concentration of the alkylsilane present in the pressed powder composition in a range from about 0.25% to about 1.5% and the concentration of the polyhydroxystearic acid is present in the pressed powder composition in a range from about 0.25% to about 3%, such as from about 0.25% to about 2% by weight.

Binding Agents

Compositions of the present invention include binding agents or "binders." The binding agents function to provide coherence to the pressed powder. One binding agent that is included in the formulation is polyhydroxystearic acid, described above. Other binding agents are optional and may include or consist of fatty compounds, silicones, water, fatty acid salts, and glycols.

By "fatty compounds" it is meant any of various fatty substances insoluble in water and including, for example, hydrocarbon based fatty substances or silicone-based fatty substances. These may be liquid or solid at room temperature and may be volatile or non-volatile. In certain embodiments, the fatty substances discussed herein are non-volatile.

Examples of suitable fatty substances include oil(s) and/or wax(es). As used herein, by "oils," it is meant compounds having a melting point of less than about 30° C. and generally insoluble in water and includes a hydrophobic moiety, such as one meeting one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy) sulfonyl moieties. In certain embodiments, the oil does not include hydroxyl moieties.

Suitable examples of compounds of oils include vegetable oils (glyceryl esters of fatty acids, monoglycerides, diglycerides, triglycerides) and fatty esters. Specific non-limiting examples include, without limitation, esters such as isopropyl palmitate, isopropyl myristate, isononyl isonanoate $C_{12}$-$C_{15}$ alkyl benzoates, caprylic/capric triglycerides, ethylhexyl hydroxystearate, silicone oils (such as dimethicone and cyclopentasiloxane), pentaerythritol tetraoctanoate and mineral oil. Other examples of oils include liquid organic ultraviolet filter commonly used for example as UV-absorbing sunscreens such as octocrylene, octyl salicylate, octyl methoxyxcinnamate, among others.

Suitable oils include volatile and/or non-volatile oils. Such oils can be any acceptable oil including but not limited to silicone oils and/or hydrocarbon oils.

According to certain embodiments, the compositions of the present invention may include one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C.

The fatty compound may include waxes. As used herein, "wax" is intended to mean a lipophilic fatty compound that is solid at room temperature (about 25° C.) and atmospheric pressure (760 mm Hg, i.e., 105 Pa), which undergoes a reversible solid/liquid change of state and which has a melting point of greater than 30° C., and in some embodiments, greater than about 55° C. up to about 120° C. or even as high as about 200° C.

The wax may change from the solid to the liquid state reversibly, and/or may have a hardness of more than 0.5 MPa at ambient temperature, and an anisotropic crystalline organization in the solid state.

The term wax may include waxes of animal origin, waxes of plant origin, waxes of mineral origin and waxes of synthetic origin. Examples of waxes of animal origin include beeswaxes, lanolin waxes and Chinese insect waxes. Examples of waxes of plant origin include rice waxes, carnauba wax, candelilla wax, ouricurry wax, cork fiber waxes, sugar cane waxes, Japan waxes, sumach wax and cotton wax. Examples of waxes of mineral origin include paraffins, microcrystalline waxes, montan waxes and ozokerites. Examples of waxes of synthetic origin include polyolefin waxes, e.g., polyethylene waxes (linear, low molecular weight polyethylene waxes), waxes obtained by Fischer-Tropsch synthesis, waxy copolymers and their esters, and silicone and fluoro waxes.

The term wax may further include high melting point hydrogenated oils of animal or plant origin. Examples include hydrogenated jojoba waxes and hydrogenated oils which are obtained by catalytic hydrogenation of fats composed of a $C_8$-$C_{32}$ linear or nonlinear fatty chain, hydrogenated sunflower oil, hydrogenated castor oil, hydrogenated copra oil, hydrogenated lanolin and hydrogenated palm oils.

By silicones it is meant those silicone fatty substances described above such as dimethicone and cyclopentasiloxane and, in particular, dimethicone having a viscosity of less than 50 centistokes (as measured by commonly used methods). Other suitable silicone binding agents include silicone elastomers (e.g, silicone rubbers, dimethicone crosspolymers).

"Fatty acid salt" binding agents include salts of fatty acids and multivalent ions. Fatty acids may have a carbon chain length from C6-C100, such as from C8 to C100, such as from C8 to C50, such as from C12-C30. Examples of fatty acid salts include magnesium stearate, zinc stearate and the like. In certain embodiments of the invention, pressed powder compositions include from about 0.5%, 1%, or 2% to about 3%, 4%, 5% or 10% of a fatty acid salt of a divalent metal.

"Glycol" binding agents include glycerin, propylene glycol, butylene glycol, hexylene glycol as well as other higher chain glycols such as caprylyl glycol.

The inventors have found that pressed powders of the present invention can be made that have reduced low or reduced fragility despite having a low concentration of binding agents. Accordingly, the concentration of the binding agents in the pressed powder composition is less than about 12% by weight. According to certain other embodiments, the concentration of the binding agents, (which definition includes the polyhydroxystearic acid) is less than about 11%, less than about 10%, or even less than about 9% or less than about 6% by weight.

Other Ingredients

Compositions of the present invention may optionally include other functional ingredients such as those that can be readily dissolved, dispersed or suspended in the composition. These may include organic particulate materials; polymers for thickening/rheology modifying; preservatives; dyes, fragrances; antioxidants; vitamins; and the like. A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

Examples of other particulate materials and particulate fillers include organic and non-mineral fillers such as polytetrafluoroethylene, vegetable starches, and the like.

Examples of polymers for thickening/rheology modifying include those particularly for oil-phase thickening or gelling effects.

According to certain other embodiments, the compositions are substantially free of tackifiers such as tackifying resins, polybutenes, and the like. By "substantially free" it is meant that the particular component is present in a concentration by weight of less than about 2% by weight, such as less than about 1% by weight, such as less than about 0.5% by weight, such as less than about 0.25% by weight.

According to preferred embodiments of the present invention, methods of reducing the fragility of a pressed powder composition. The methods include adding at least one alkylsilane-coated mineral and polyhydroxystearic acid to a base powder composition. The base powder composition generally includes at least one mineral other than the alkylsilane coated mineral. The methods further include forming a pressed powder composition that includes at least about 80% by weight of a mineral portion wherein the mineral portion includes polyhydroxystearic acid and at least one alkylsilane-coated mineral; and the pressed powder composition includes less than about 12% by weight of binding agents.

According to certain aspects of the invention, the pressed powder composition is made by using an alkysilane-coated mineral, and, more particularly a mineral that is itself only-coated with alkylsilane. The alkylsilane-coated mineral may be blended with optional other minerals such as synthetic mica, among others to form a powder portion. Binders including polyhydroxystearic acid and optional silicones, glycol, multivalent fatty acid salts and/or water may be added—to form a mixture of at least powder and binders, i.e., a powder-binder composition. Other optional ingredients such as preservatives, dyes and the like may be included. Unlike embodiments in which the polyhydroxystearic acid is coated onto the alkylsilane-coated mineral, when there is no preformed polyhydroxystearic acid coating on the alkylsilane-coated mineral, as provided, no additional high temperature drying step is required to dry the polyhydroxystearic acid. Accordingly, in certain embodiments, a method of making a pressed powder includes the step of adding polyhydroxystearic acid to a powder portion wherein the powder portion includes at least one mineral coated with alkylsilane to form a powder-binder composition; and mechanically pressing the powder-binder composition without previously heating the powder-binder composition to a high temperature. By "high temperature," it is meant a temperature of at least 50° C., such as at least about 75° C., such as at least about 100° C.

According to preferred embodiments of the present invention, methods of making up, treating, caring for the keratinous materials, especially skin and in particular the eyes by applying compositions of the present invention to the keratinous material in an amount sufficient to treat, care for and/or make up the keratinous material are provided. According to yet other preferred embodiments, methods of shadowing the eyes include applying the pressed powder to eyelids and/or skin around the eyes. Compositions may be applied using any variety of conventional applicators.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Example I—Drop Testing for Compositions with Various Iron Oxides

Six compositions were prepared. All the compositions shared in common of about 48% iron oxide color pigment; about 38% of various "other" minerals (including synthetic mica); about 8% binders (including polyhydroxystearic acid and a divalent salt of a fatty acid), and about 6% other ingredients. The coating on the iron oxide was varied, as indicated in Table 1 below.

The first, Comparative Example Comp 1, was prepared 200 grams by combining minerals and fillers and mixing for about 2 minutes; adding liquids and mixing again for about a minute; and sifting through a mesh. Pressing was done using a hydraulic manual press and holding for 3 seconds. All samples were pressed, 3.5 grams, into a rectangular pan. A DROP-INDUCED PRODUCT LOSS TEST was performed by dropping the pan 8 times from a fixed height onto a hard surface. Initial weight was recorded and again after 3, 5 and 8 drops.

As a measure of fragility and the loss of product due to breakage, Drop-Induced Product Loss (in percent) was calculated as (Initial weight of sample-Weight of Sample at defined number of drops)/Initial Weight, and recorded below. As noted above and in the data, according to certain embodiments, the inventive samples have a Drop-Induced Product Loss (in percent) at 3 drops that is at least 50% less than when compared with a similar (or identical) formula where the alkylsilane-coated mineral is substituted with an uncoated mineral of the same mineral substrate.

For Comparative Example Comp 1, uncoated iron oxide was used as the color pigment. The second, Comparative Example Comp 2, was prepared in a similar manner. Another uncoated iron oxide was used. The Inventive Example Ex 1, was prepared in a similar manner but using an iron oxide coated with triethoxycaprylylsilane and polyhydroxystearic acid. Comparative Example Comp 3 used an iron oxide coated only with triethoxycaprylylsilane. Comparative Example Comp 4 used an iron oxide coated with dimethicone. Comparative Example Comp 5 used an iron oxide coated with aluminum hydroxide and disodium stearoyl glutamate.

TABLE 1

Drop Test Comparison of Compositions with Varying Iron Oxides

| | DROP-INDUCED PRODUCT LOSS (weight %) | | | | | |
|---|---|---|---|---|---|---|
| | Comp 1 | Comp 2 | Ex 1 | Comp 3 | Comp 4 | Comp 5 |
| 3 drops | 19.08 | 24.39 | 8.05 | 11.30 | 15.54 | 19.04 |
| 5 drops | 41.08 | 49.15 | 19.91 | 47.90 | 41.18 | 42.44 |
| 8 drops | 80.99 | 86.36 | 40.31 | 89.68 | 87.69 | 87.56 |

The results indicate that it is surprisingly possible to reduce the fragility of pressed powder compositions with iron oxide by replacing uncoated iron oxide with iron oxide that is coated with both alkylsilane and polyhydroxystearic acid in a composition less than 12% binder.

Example II—Drop Testing for Compositions with Various Titanium Dioxides

Four compositions were prepared. All the compositions shared in common of about 7% titanium dioxide; about 79% of various "other" minerals (including synthetic mica); about 8% binders (including polyhydroxystearic acid and divalent salt of fatty acid), and about 6% other ingredients. The coating on the titanium dioxide was varied, as indicated in Table 2 below.

The compositions were prepared in a manner similar to those in Example II and evaluated in a DROP-INDUCED PRODUCT LOSS TEST also in a similar manner. Comparative Example Comp 11 utilized uncoated titanium dioxide, Example Ex 11 utilized a titanium dioxide coated with triethoxycaprylylsilane and polyhydroxystearic acid. Comparative Example Comp 12 utilized a titanium dioxide coated only with triethoxycaprylylsilane; Comparative Example Comp 13 utilized titanium dioxide coated with aluminum hydroxide and disodium stearoyl glutamate.

TABLE 2

Drop Test Comparison of Compositions with Varying Titanium Dioxides

| | Comp 11 | Ex 11 | Comp 12 | Comp 13 |
|---|---|---|---|---|
| | DROP-INDUCED PRODUCT LOSS (weight %) | | | |
| 3 drops | 1.34 | 0.32 | 2.19 | 1.53 |
| 5 drops | 18.3 | 1.73 | 3.91 | 5.35 |
| 8 drops | 31.77 | 6.69 | 14.72 | 12.41 |

The results indicate that it is surprisingly possible to reduce the fragility of pressed powder compositions including less than about 12% binder and titanium dioxide, by replacing uncoated titanium dioxide with titanium dioxide that is coated with both alkylsilane and polyhydroxystearic acid.

The results are especially surprising, as the improvement in Drop-Induced Product Loss is, in certain aspects, at least as good as the improvement Example I. In Example II the alkylsilane-coated mineral is a small fraction (only 7% by weight) of the pressed powder composition.

Example III—Drop Testing for Compositions with Various Iron Oxides

In order to observe whether adding polyhydroxystearic acid added separately to the composition (rather than coating it directly onto the iron oxide), six compositions were prepared and tested. Similar to those in Example I, the compositions shared in common of about 48% iron oxide color pigment; about 38% of various "other" minerals (uncoated or pearlescent pigments); about 8% binders, and about 6% other ingredients. The coating on the iron oxide was varied, as indicated in Table 1 below.

The compositions were prepared in a manner similar to those in Example I and evaluated in a DROP-INDUCED PRODUCT LOSS TEST also in a similar manner.

Comparative Example 2 (uncoated) is shown for comparison purposes. For Inventive Example Ex 31, the iron oxide was coated with triethoxycaprylylsilane and polyhydroxystearic acid. For Inventive Example Ex 32, the iron oxide was coated with only triethoxycaprylylsilane. However, one percent polyhydroxystearic acid was separately added to the composition. Inventive Example Ex 33, the iron oxide was identical to Inventive Example Ex 32 but, two percent polyhydroxystearic acid was separately added to the composition. Inventive Examples Ex 34 and Ex 35 were identical to Inventive Examples Ex 32 and Ex 33 except a different iron oxide was used as the mineral substrate. Inventive Example Ex 36 was identical to Inventive Example Ex 35 but, four percent polyhydroxystearic acid was separately added to the composition.

portion with alkylsilane-coated iron oxide to form a powder-binder composition. The powder-binder composition is thereby formed without having to heat the powder-binder composition to a high temperature to dry the polyhydroxystearic acid.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. accordingly, the description is not intended to limit the invention to the form disclosed herein. Also, it is intended to the appended claims to construed to include alternative embodiments.

What is claimed is:

1. A method of forming a pressed powder composition, wherein the method comprises:
    forming a powder-binder composition by adding polyhydroxystearic acid to a powder portion, wherein the powder portion comprises at least one mineral coated with alkylsilane, the at least one mineral free of a preformed polyhydroxystearic acid coating; and
    mechanically pressing the powder-binder composition without previously heating the powder-binder composition.

2. The method of claim 1, further comprising forming the pressed powder composition such that the pressed powder composition comprises about 5% by weight to about 40% by weight of the at least one alkylsilane-coated mineral.

3. The method of claim 1, wherein the at least one a mineral coated with alkylsilane comprises a mineral sub-

TABLE 3

Drop Test Comparison of Compositions with Varying Iron Oxides

|  | Comp 2 Uncoated | Ex 31 Coated with triethoxy-caprylylsilane and polyhydroxystearic acid | Ex 32 Coated with triethoxy-caprylylsilane; 1% PHSA added | Ex 33 Coated with triethoxy-caprylylsilane; 2% PHSA added | Ex 34 Coated with triethoxy-caprylylsilane; 1% PHSA added | Ex 35 Coated with triethoxy-caprylylsilane; 2% PHSA added | Ex 36 Coated with triethoxy-caprylylsilane; 4% PHSA added |
|---|---|---|---|---|---|---|---|
| 3 drops | 24.39 | 8.05 | 6.12 | 6.89 | 2.03 | 2.28 | 1.11 |
| 5 drops | 49.15 | 19.91 | 17.41 | 27.89 | 5.86 | 6.53 | 5.17 |
| 8 drops | 86.36 | 40.31 | 53.05 | 59.33 | 16.91 | 17.92 | 19.59 |

The results indicate that it is surprisingly possible to reduce the fragility of pressed powder compositions with iron oxide even further by replacing uncoated iron oxide with iron oxide that is coated with both alkylsilane and adding polyhydroxystearic acid separately to the composition rather than coating the iron oxide with both alkylsilane polyhydroxysteraic acid. In this example, Examples 32-36 were formed by adding polyhydroxystearic acid to a powder strate selected from iron oxide, titanium dioxide, talc, natural or synthetic mica, silica, borosilicate, and combinations thereof.

4. The method of claim 1, wherein the at least one a mineral coated with alkylsilane is alkylsilane-coated iron oxide.

5. The method of claim 1, further comprising forming the pressed powder composition such that the pressed powder composition comprises at least about 11% of a combined weight percentage of minerals having substrates selected from titanium dioxide and iron oxide.

6. The method of claim 1, wherein the alkylsilane is triethoxycaprylylsilane.

7. The method of claim 1, further comprising forming the pressed powder composition such that the pressed powder composition comprises at least about 80% by weight of a mineral portion.

8. The method of claim 1, wherein the pressed powder composition comprises synthetic mica.

9. The method of claim 1, wherein forming the powder-binder composition further comprises adding at least one additional binding agent to the powder portion, the at least one additional binding agent selected from a group consisting of fatty compounds, water, fatty acid salts, and glycols.

10. The method of claim 9, wherein the sum of the amount of the first binding agent and the at least one additional binding agent is less than about 12% by weight of the pressed powder composition.

* * * * *